United States Patent [19]
Kurita et al.

[11] Patent Number: 5,908,828
[45] Date of Patent: Jun. 1, 1999

[54] SYNTHETIC PEPTIDE DERIVATIVES AND THE SALTS THEREOF

[75] Inventors: Takashi Kurita, Suita; Tomoaki Matsumoto, Kawagoe; Reiko Kikuno, Tokorozawa; Yoko Otawara-Hamamoto, Kamifukuoka, all of Japan; Gerhard Breipohl, Frankfurt, Germany

[73] Assignee: Hoechst Japan Limited, Tokyo, Japan

[21] Appl. No.: 08/497,599

[22] Filed: Jun. 30, 1995

[30] Foreign Application Priority Data

Jul. 4, 1994 [JP] Japan .................................. 6-184203

[51] Int. Cl.⁶ ........................... A61K 38/16; C07K 14/00
[52] U.S. Cl. ............................. 514/12; 514/13; 530/323; 530/324; 530/326
[58] Field of Search ...................... 530/323, 324, 530/326; 514/12, 13

[56] References Cited

FOREIGN PATENT DOCUMENTS

| 0626451A2 | 5/1994 | European Pat. Off. . |
| WO 93/00049 | 1/1993 | WIPO . |
| WO 93/09229 | 5/1993 | WIPO . |

OTHER PUBLICATIONS

E. A. Wang et al. Proc. Natl. Acad. Sci. U.S.A., 87: 2220–2224 (1990).
Y. Takuwa et al., Biochem. Biophys. Res. Communi., 174 (1): 96–101 (1991).
J. Pfeilschifter et al., Endocrinology, 121 (1): 212–218 (1987).
K. Boström et al., J. Clin. Invest., 91: 1800–1809 (1993).
H. Kodama et al., Jap. J. Oral Biol., 23: 899–901 (1981).
G. A. Rodan et al., in "Calcium regulating hormones and bone metabolism." Elsevier Science Publishers B.V. pp. 183–196 (1992).
H. Kawaquchi et al., Spine, 17 (3S): S 33–S 36 (1992).

*Primary Examiner*—Cecilia Tsang
*Assistant Examiner*—Anish Gupta
*Attorney, Agent, or Firm*—Finnegan, Henderson, Farabow, Garrett & Dunner, L.L.P.

[57] ABSTRACT

The present invention provides synthetic peptide derivatives represented by the formula $$P^1\text{-}R^1\text{-}P^2$$

wherein $P^1$ is a peptide having an amino acid sequence in the SEQ ID NO.:1 of the Sequence Listing, or analogues thereof; $P^2$ is a peptide having an amino acid sequence in the SEQ ID NO.:2 of the Sequence Listing, or analogues thereof; $R^1$ denotes a linker with a property that does not interfere with the activity of the each peptide $P^1$ and $P^2$ to bind N-terminal end of the peptides $P^1$ and $P^2$.

The present invention also provides a pharmaceutical composition for the treatment of bone related diseases comprising said peptide derivatives, or a therapeutically acceptable salt thereof, and a pharmaceutically acceptable carrier.

The present invention also provides a method of treating bone related diseases in a mammal comprising administering thereto an effective amount of said peptide derivatives, or therapeutically acceptable salts thereof.

8 Claims, 1 Drawing Sheet

FIG. 1

| | | |
|---|---|---|
| TGF-ß1 | 23 DFRKDLGWK- WIHEPKGY | 39 |
| TGF-ß2 | 23 DFKRDLGWK- WIHEPKGY | 39 |
| TGF-ß3 | 23 DFRQDLGWK- WVHEPKGY | 39 |
| BMP-2 | 22 DF-SDVGWND WIVAPPGY | 38 |
| BMP-3 | 41 DF-ADIGWSE WIISPKSF | 57 |
| BMP-4 | 24 DF-SDVGWND WIVAPPGY | 40 |
| BMP-5 | 39 SF-RDLGWQD WIIAPEGY | 55 |
| BMP-6 | 39 SF-QDLGWQD WIIAPKGY | 55 |
| BMP-7 | 10 SF-RDLGWQD WIIAPEGY | 26 |
| BMP-8 | 46 SF-QDLGWLD WVIAPQGY | 62 |
| BMP-9 | 16 NF-EDIGWDS WIIAPKEY | 32 |
| MP52 | 27 NF-KDMGWDD WIIAPLEY | 43 |

FIG. 2

| | | |
|---|---|---|
| TGF-ß1 | 59 SKVLALYN-- QHNPGASAAP | 76 |
| TGF-ß2 | 59 SRVLSLYN-- TINPEASASP | 76 |
| TGF-ß3 | 59 STVLGLYN-- TLNPEASASP | 76 |
| BMP-2 | 61 AIVQTLVNS- --VNSKIPKA | 77 |
| BMP-3 | 80 ATIQSIVRA- VGVVPGIPEP | 98 |
| BMP-4 | 64 AIVQTLVNS- --VNSSIPKA | 80 |
| BMP-5 | 78 AIVQTLVHL- -MFPDHVPKP | 95 |
| BMP-6 | 78 AIVQTLVHL- -MNPEYVPKP | 95 |
| BMP-7 | 49 AIVQTLVHF- -INPETVPKP | 66 |
| BMP-8 | 85 AILQSLVHL- -MKPNAVPKA | 102 |
| BMP-9 | 55 AIVQTLVHL- -KFPTKVGKA | 72 |
| MP52 | 66 AVIQTLMNS- -MDPESTPPT | 83 |

SEQUENCE LISTING (1) GENERAL INFORMATION:

(iii) NUMBER OF SEQUENCES: 26

(2) INFORMATION FOR SEQ ID NO:1:

(i) SEQUENCE CHARACTERISTICS:
       (A) LENGTH: 17 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO:1:

Asp Phe Ser Asp Val Gly Trp Asn Asp Trp Ile Val Ala Pro Pro Gly
   1               5                   10                  15

Tyr (2) INFORMATION FOR SEQ ID NO:2:

(i) SEQUENCE CHARACTERISTICS:
       (A) LENGTH: 17 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO:2:

Ala Ile Val Gln Thr Leu Val Asn Ser Val Asn Ser Lys Ile Pro Lys
   1               5                   10                  15

Ala (2) INFORMATION FOR SEQ ID NO:3:

(i) SEQUENCE CHARACTERISTICS:
       (A) LENGTH: 17 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO:3:

Asp Phe Arg Lys Asp Leu Gly Trp Lys Trp Ile His Glu Pro Lys Gly
   1               5                   10                  15

Tyr (2) INFORMATION FOR SEQ ID NO:4:

(i) SEQUENCE CHARACTERISTICS:
       (A) LENGTH: 17 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO:4:

Asp Phe Lys Arg Asp Leu Gly Trp Lys Trp Ile His Glu Pro Lys Gly
   1               5                   10                  15

Tyr (2) INFORMATION FOR SEQ ID NO:5:

(i) SEQUENCE CHARACTERISTICS:
        (A) LENGTH: 17 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:5:

Asp Phe Arg Gln Asp Ile Leu Trp Lys Trp Val His Glu Pro Lys Gly
    1               5                  10                  15

Tyr (2) INFORMATION FOR SEQ ID NO:6:

(i) SEQUENCE CHARACTERISTICS:
        (A) LENGTH: 17 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:6:

Asp Phe Ser Asp Val Gly Trp Asn Asp Trp Ile Val Ala Pro Pro Gly
    1               5                  10                  15

Tyr (2) INFORMATION FOR SEQ ID NO:7:

(i) SEQUENCE CHARACTERISTICS:
        (A) LENGTH: 17 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:7:

Asp Phe Ala Asp Ile Gly Trp Ser Glu Trp Ile Ile Ser Pro Lys Ser
    1               5                  10                  15

Phe (2) INFORMATION FOR SEQ ID NO:8:

(i) SEQUENCE CHARACTERISTICS:
        (A) LENGTH: 17 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:8:

Asp Phe Ser Asp Val Gly Trp Asn Asp Trp Ile Val Ala Pro Pro Gly
    1               5                  10                  15

Tyr (2) INFORMATION FOR SEQ ID NO:9:

(i) SEQUENCE CHARACTERISTICS:
        (A) LENGTH: 17 amino acids
        (B) TYPE: amino acid
        (C) STRANDEDNESS: single
        (D) TOPOLOGY: linear

```
        (ii) MOLECULE TYPE: peptide (xi) SEQUENCE DESCRIPTION: SEQ ID NO:9:

Ser Phe Arg Asp Leu Gly Trp Gln Asp Trp Ile Ile Ala Pro Glu Gly
    1               5                  10                  15

Tyr (2) INFORMATION FOR SEQ ID NO:10:

(i) SEQUENCE CHARACTERISTICS:
            (A) LENGTH: 17 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:10:

Ser Phe Gln Asp Leu Gly Trp Gln Asp Trp Ile Ile Ala Pro Lys Gly
    1               5                  10                  15

Tyr (2) INFORMATION FOR SEQ ID NO:11:

(i) SEQUENCE CHARACTERISTICS:
            (A) LENGTH: 17 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:11:

Ser Phe Arg Asp Leu Gly Trp Gln Asp Trp Ile Ile Ala Pro Glu Gly
    1               5                  10                  15

Tyr (2) INFORMATION FOR SEQ ID NO:12:

(i) SEQUENCE CHARACTERISTICS:
            (A) LENGTH: 17 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:12:

Ser Phe Gln Asp Leu Gly Trp Leu Asp Trp Val Ile Ala Pro Gln Gly
    1               5                  10                  15

Tyr (2) INFORMATION FOR SEQ ID NO:13:

(i) SEQUENCE CHARACTERISTICS:
            (A) LENGTH: 17 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:13:

Asn Phe Glu Asp Ile Gly Trp Asp Ser Trp Ile Ile Ala Pro Lys Glu
    1               5                  10                  15

Tyr
```

(2) INFORMATION FOR SEQ ID NO:14:

(i) SEQUENCE CHARACTERISTICS:
        (A) LENGTH: 17 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:14:

```
Asn Phe Lys Asp Met Gly Trp Asp Asp Trp Ile Ile Ala Pro Leu Glu
1               5                  10                  15

Tyr
```

(2) INFORMATION FOR SEQ ID NO:15:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:15:

```
Ser Lys Val Leu Ala Leu Tyr Asn Gln His Asn Pro Gly Ala Ser Ala
1               5                  10                  15

Ala Pro
```

(2) INFORMATION FOR SEQ ID NO:16:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:16:

```
Ser Arg Val Leu Ser Leu Tyr Asn Thr Ile Asn Pro Glu Ala Ser Ala
1               5                  10                  15

Ser Pro
```

(2) INFORMATION FOR SEQ ID NO:17:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:17:

```
Ser Thr Val Leu Gly Leu Tyr Asn Thr Leu Asn Pro Glu Ala Ser Ala
1               5                  10                  15

Ser Pro
```

(2) INFORMATION FOR SEQ ID NO:18:

(i) SEQUENCE CHARACTERISTICS:
        (A) LENGTH: 17 amino acids
        (B) TYPE: amino acid
        (C) STRANDEDNESS: single (D) TOPOLOGY: linear (ii) MOLECULE TYPE: peptide (xi) SEQUENCE DESCRIPTION: SEQ ID NO:18:

Ala Ile Val Gln Thr Leu Val Asn Ser Val Asn Ser Lys Ile Pro Lys
    1               5                  10                  15

Ala (2) INFORMATION FOR SEQ ID NO:19:

(i) SEQUENCE CHARACTERISTICS:
        (A) LENGTH: 19 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:19:

Ala Thr Ile Gln Ser Ile Val Arg Ala Val Gly Val Val Pro Gly Ile
    1               5                  10                  15

Pro Glu Pro (2) INFORMATION FOR SEQ ID NO:20:

(i) SEQUENCE CHARACTERISTICS:
        (A) LENGTH: 17 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:20:

Ala Ile Val Gln Thr Leu Val Asn Ser Val Asn Ser Ser Ile Pro Lys
    1               5                  10                  15

Ala (2) INFORMATION FOR SEQ ID NO:21:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:21:

Ala Ile Val Gln Thr Leu Val His Leu Met Phe Pro Asp His Val Pro
    1               5                  10                  15

Lys Pro (2) INFORMATION FOR SEQ ID NO:22:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:22:

Ala Ile Val Gln Thr Leu Val His Leu Met Asn Pro Glu Tyr Val Pro
    1               5                  10                  15

-continued

```
    Lys Pro (2) INFORMATION FOR SEQ ID NO:23:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:23:

Ala Ile Val Gln Thr Leu Val His Phe Ile Asn Pro Glu Thr Val Pro
    1               5                  10                  15

Lys Pro (2) INFORMATION FOR SEQ ID NO:24:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:24:

Ala Ile Leu Gln Ser Leu Val His Leu Met Lys Pro Asn Ala Val Pro
    1               5                  10                  15

Lys Ala (2) INFORMATION FOR SEQ ID NO:25:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:25:

Ala Ile Val Gln Thr Leu Val His Leu Lys Phe Pro Thr Lys Val Gly
    1               5                  10                  15

Lys Ala (2) INFORMATION FOR SEQ ID NO:26:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:26:

Ala Val Ile Gln Thr Leu Met Asn Ser Met Asp Pro Glu Ser Thr Pro
    1               5                  10                  15

Pro Thr
```

SYNTHETIC PEPTIDE DERIVATIVES AND THE SALTS THEREOF

BACKGROUND OF THE INVENTION

1. Field of the Invention

This invention provides novel synthetic peptide derivatives and the salts thereof with pharmacological activity. The synthetic peptide derivatives and the salts thereof of this invention show bone morphogenetic protein antagonist like activity. This invention with bone morphogenetic protein antagonist activity is useful for treating and preventing bone metabolic diseases accompanied by ectopic calcification, ectopic bone formation or calcification, such as neural osteosis, ectopic ossification by postoperative stress, traumatic ossific myositis, ossification by oxygen supply deficit, osteogenic tumor, ligamentum longitudinale postreius osteosis (OPLL) and arterial sclerosis.

Bone morphogenetic protein (BMP) is a protein with bone morphogenetic activity in decalcified bone tissue. Although the isolation of BMP had been worked on energetically since the 1970s, it did not succeeded in isolating as a single protein. Gene cloning of BMP was performed by Wozney in 1989 by molecular biological method, using the amino acid sequences derived from unknown peptides which were separated from treating the fraction having BMP activities with an enzyme. The gene was immediately introduced to the animal cultured cells, and the activity of the protein expressed was measured in vivo, and BMP activity in the protein was proved (Wang, E. A. et al., (1990) Proc. Natl. Acad. Sci. USA, vol.87, p.2220–2224). Continuing the protein cloning of similar activities utilizing homology, several numbers of the proteins, that is from BMP-2 to BMP-9 have been identified so far. Those proteins belong to TGF-β gene super family and are confirmed to have the activity to cause ectopic ossification in vivo, basically. Ossification caused by BMP is said to be internal cartilaginous and it seems to reproduce the formation of long bone at an embryonal stage. Therefore, BMP itself can be used as a medical agent for the treatment to compensate the bone deficit.

2. Description of the Prior Art

On the other hand, since BMP genes were reported, the specific antibodies against BMP were prepared and BMPs were also existed in critical parts of ectopic calcification, ectopic ossification and so on, which have not had any treatment so far, there seem some possibilities of the relationship between BMPs and those diseases. Recently it is evident that BMP is existed or included in diseases such as neural osteosis, ectopic ossification by postoperative stress, traumatic ossific myositis, ossification by oxygen supply deficit, osteogenic tumor, specified as refractory diseases such as ossification of the posterior longitudinal ligament (OPLL) (Spine, 17-3S, S33, 1992) and calcification part of arterial sclerosis (J. Clin. Invest., vol. 91, p.1800, 1993). In addition, the major symptoms of pseudomalignant heterotopic ossification (PHO), pseudomalignant osseous tumor, myosistis ossificans circumscripta are ache and the existence of the mass in hard tissue of the muscle. Though the causes of these diseases are still unknown in detail, BMP seems to have a relation to the existence in hard tissue of the muscle of the patients. It is considered that BMP existed in the tissue which is not supposed to exist, acts on autocrine and bone like hard tissue is formed.

There is no effective treatment for OPLL by now. If the oppressive neural symptom is serious, excision is occurred. However prognosis is not so good. There is no treatment for calcification of artery, either. It seems that suppression of BMP existence may be one of the major treatments for these diseases. Another treatment, such as administration of BMP antagonists, also seems effective.

Therefore, it was desired eagerly the effective method of treatment for above described diseases related to bone like tissue formation. BMP receptors, neutralized antibodies against BMP and the peptide according to BMP's binding position are thought to have BMP antagonist like activity.

DETAILED DESCRIPTION OF THE INVENTION

Many investigations have been made on the structure active relations of BMP. However it has not been known that which region of matured BMP-2 is related to bind with the receptors, nor which fragment of BMP-2 is able to bind to its receptors.

For the purpose of designing a peptide to have the binding ability to the receptors as BMP antagonists, we estimated a three-dimensional structure of BMP-2 based on that of TGF-β2 which is a homologous protein to BMP-2, and then estimated the receptor binding region of BMP-2.

We considered that the active protein of BMP was a dimer, and that the receptor binding region of the protein such as BMP seemed to be the exposure of the external region of protein molecule. Then when BMP-2 formed a dimer, the receptor binding region was expected to be formed of two neighboring peptide domain (The position number of matured form of BMP-2 is from Asp of position 22 to Tyr of position 38 and from Ala of position 61 to Ala of position 77 on each molecule, respectively). Based on the consideration, we designed a peptide derivative having these two peptides bound to a linker that was able to connect with these two peptides and keeping a suitable distance between the peptides to bind with the receptors. Suitable linkers are bivalent organic group containing carboxyl group on both ends and consists the peptide derivative similar to the estimated steric structure of BMP-2.

The synthetic peptide derivatives of this invention are represented by the following formula.

$$P^1-R^1-P^2$$

$P^1$ is a peptide having amino acid sequence as shown in the SEQ ID NO.:1 of the Sequence Listing, or analogues thereof; $p^2$ is a peptide having an amino acid sequence as shown in the SEQ ID NO.:2 of the Sequence Listing, or analogues thereof; $R^1$ denotes a linker that bind with N-terminal end of each peptide $P^1$ and $P^2$. Any linking group $R^1$ can be used, provided that it does not interfere with the activity of the peptide segments $P^1$ and $P^2$.

Suitable linking groups can be maleinimido based linkers formula I or disulfide based linkers of formula II, for example;

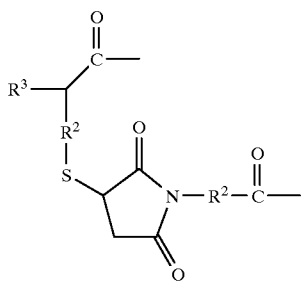

[formula I]

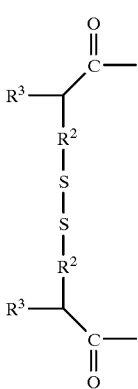

[formula II]

wherein $R^2$ is independently $C_1$–$C_6$ alkylene, $C_6$–$C_9$ cycloalkylalkylene or $C_7$–$C_9$ phenylalkylene and $R^3$ is preferably $CH_3CO—NH—$ or either one of hydrogen, alkyl, aryl, alkanoylamino or aryloylamino.

For linker $R^1$ shown in the former formula, $C_1$–$C_6$ alkylene may include methylene, ethylene, propylene or butylene, $C_6$–$C_9$ cycloalkylalkylene may include cyclohexylmethylene-4-yl or cyclohexylethylene-3-yl, $C_7$–$C_9$ phenylalkylene may include phenylmethylene or phenylethylene. More preferably group $R^2$ is methylene or methylene-4-cyclohexyl groups.

Preferable examples of linkers of this invention are shown in the following formulas:

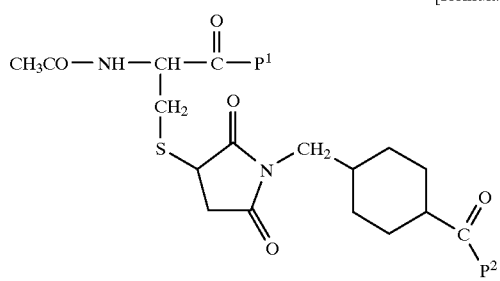

[formula III]

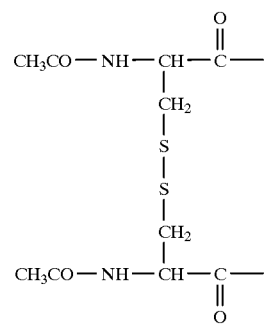

[formula IV]

Analogues of each peptide of $P^1$ and $P^2$ means modifications of amino acid sequence, that is, substituted, deleted or added by one or more amino acids. Therefore, these analogues may include the protein having the same amino acid sequence of the synthetic peptide derivative of this invention as a part of said protein. Moreover, these analogues may also include the protein with an essential region of amino acid sequence enough to hold the essential property of said synthetic peptide derivative of this invention. Such proteins, for examples, have at least the substantial region of the amino acid sequence of said synthetic peptide derivative, more preferably having amino acid at least more than 85%, or more than 90%.

These analogues of this invention may also include something called a mutant which is improved its property by the modification of amino acid sequences.

The analogues of the synthetic peptide derivatives of this invention may also include the proteins which are fused with other proteins. Therefore, this invention also covers fused proteins.

Furthermore, these analogues may also include the proteins having the amino acid sequence of BMP group or TGF-β group. For instance, preferable examples for the analogue of peptide $P^1$ (SEQ ID NO:3 through SEQ ID NO:14) are shown in FIG. 1, and preferable examples for the analogues of the peptide P2 (SEQ ID NO:15 through SEQ ID NO:26) are shown in FIG. 2.

These peptides are corresponded to the binding region of the BMP-2 receptors, and may be expected to have the activity as the peptide $P^1$, the peptide $P^2$ derived from BMP-2.

The amino acid sequences of these synthetic peptides may be D-form, L-form or racemate, if not indicated.

This invention is related to the novel synthetic peptide derivatives shown by the above mentioned amino acid sequence, their analogues and pharmaceutically acceptable salts thereof.

BMP-2 antagonist-like activity of the present synthetic peptide derivatives was assayed by way of cultured MC3T3-E1 cells which were established from mouse calvaria having osteoblast-like property, by Kodama et al. (Kodama, H. et al. (1981) Jpn. J Oral. Biol., vol.23, p.899). The cultured MC3T3-E1 cells were prepared according to Takuwa et al. (Takuwa, Y. et al., (1991) Biochem.

Biophys. Res. Comuni., vol. 174, p.96–101), $5\times10^4$ cells/$cm^2$ of the cultured cells in serum-free α-MEM culture broth containing serum albumin were treated with various concentrations of synthetic peptide derivatives of this invention and recombinant human BMP-2 (rh-BMP-2) for 2 days so as to assay alkaline phosphatase (ALPase) activity in the cells by colorimetry on p-nitrophenyl phosphate. ALPase is often used as an indicator enzyme for differentiation and maturity of osteoblasts and chondrocytes (Pfeilschifter, J., et al., Endocrinology (1987), vol. 121, p212–218; Rodan, G. A., et al., calcium regulating hormones and bone metabolism, Elsevir Science Publishers B.V., (1992), p 183–196).

The present synthetic peptide derivatives inhibited ALPase activity in MC3T3-E1 cells, with osteoblast-like property which were promoted by recombinant human BMP-2 (rh-BMP-2), with $2 \times 10^{-9}$ to $2 \times 10^{-6}$M dose dependently.

The synthetic peptide derivatives, their analogues and pharmaceutically acceptable salts thereof of this invention are an effective treating agent to inhibit the symptoms of OPLL, arterial sclerosis, and is a treatment for BMP expressed bone or cartilage tumor or other bone metabolic diseases. It can be administered by phleboclysis and intramuscularly. Phleboclysis and intravenous drips are also possible for administration.

For therapeutic administrations, the synthetic peptide derivatives according to the present invention are used in the form of pharmaceutical preparations which contain said peptide derivatives in admixture with a pharmaceutically acceptable carriers such as an organic or inorganic solid or liquid excipients suitable for an administration.

For example, it can be prepared as a powder preparation for injection. In this case, one or more than two kinds of water soluble excipients such as mannitol, sugar, milk sugar, maltose, glucose and fructose may be added to the agent and dissolved in water. And after putting the mixture into vials or ampoules, they are frozen, dried and then sealed to be an injection preparation.

Although the adult clinical administration dosage for a day may vary from and also depend on ages, weigh, conditions of patients and so on, it is usually 1–500 mg for these peptide derivatives.

BRIEF EXPLANATION OF FIGURES

FIG.1 shows some examples of analogues of peptide $P^1$ of this invention by one letter symbol of amino acids. The left side of each peptide indicates the protein name having the amino acid sequence, and the number at both side of the peptide ends indicate the amino acid position number of the protein. The symbol "–" in the peptide chain shows the lack of corresponding amino acid when aligned and compared with consensus of peptide $P^1$. In FIG. 1, the amino acid sequence on line 1 corresponds to (SEQ ID NO:3), line 2 corresponds to (SEQ ID NO:4), line 3 corresponds to (SEQ ID NO:5), line 4 corresponds to (SEQ ID NO:6), line 5 corresponds to (SEQ ID NO:7), line 6 corresponds to (SEQ ID NO:8), line 7 corresponds to (SEQ ID NO:9), line 8 corresponds to (SEQ ID NO:10), line 9 corresponds to (SEQ ID NO:11), line 10 corresponds to (SEQ ID NO:12), line 11 corresponds to (SEQ ID NO:13), line 12 corresponds to (SEQ ID NO:14).

FIG. 2 shows some examples of analogues of peptide $P^2$ of this invention by one letter symbol of amino acids. The left side of each peptide indicates the protein name having the amino acid sequence, and the number at both sides of the peptide ends indicate the amino acid position number of the protein. The symbol "–" in the peptide chain shows the lack of corresponding amino acid when aligned and compared with consensus of peptide $P^2$. In FIG. 2, the amino acid sequence on line 1 corresponds to (SEQ ID NO:15), line 2 corresponds to (SEQ ID NO:16), line 3 corresponds to (SEQ ID NO:17), line 4 corresponds to (SEQ ID NO:18), line 5 corresponds to (SEQ ID NO:19), line 6 corresponds to (SEQ ID NO:20), line 7 corresponds to (SEQ ID NO:21), line 8 corresponds to (SEQ ID NO:22), line 9 corresponds to (SEQ ID NO:23), line 10 corresponds to (SEQ ID NO:24), line 11 corresponds to (SEQ ID NO:25), line 12 corresponds to (SEQ ID NO:26).

EXAMPLES

The present invention is described in detail by the examples written below. Though this invention is not restricted to these examples.

Example 1

Synthesis of Peptide Derivatives

The present peptide derivatives were synthesized by means of solid-phase method by using 430 A Peptide Synthesizer (Applied Biosystems Co. Ltd.). All the reagents and buffers were purchased from Applied Biosystems Co. except p-methylbenzhydrylamine resin which was purchased from Kokusan Chemical Co. for the use of a solid-phase resin. N-9-fluorenylmethoxycarbonyl-[(5-carboxylatoethyl-2,4-dimethyloxyphenyl)-4'-methoxyphenyl]methylamine was used as a linker, and linked to the former resin (0.52 mmol/g). α-amino group of each amino acid (1 mmol/g) was protected by Fmoc (9-flurorenyloxycarbonyl) group. Fmoc-Trp (Boc)-OH was purchased from Nova Biochem, Inc., SMCC (succinimidyl 4-( N-maleimidomethyl)-cyclohexane-1-carboxylate) was purchased from Pias Inc. and 4-methylmercaptophenol was purchased from Aldrich Chemicals Inc.

ε-amino group of Lys was protected by Boc (tert-butyloxycarbonyl) group, β-hydroxy group of Ser, β-hydroxy group of Thr, p-benzylhydroxy group of Tyr, and β-carboxyl of Asp were protected by tert-butyl group, β-amido group of Asn, γ-amido of Gln and β-mercapto group of Cys were protected by trityl group.

(1) Synthesis of Fragment $P^2$ in SEQ ID NO.:2 of the Sequence Listing

The peptide from C-terminal to the position 17, Ala, was synthesized by the Peptide Synthesizer. 110 mg of peptide-resin was suspended in 1 ml of N-methylpyrolindone (NMP) and 50 mg of SMCC dissolved in 0.3 ml of NMP was added in order to introduce 4-(N-maleimidomethyl) cyclohexane 1-carbonyl group to N-terminal of the peptide. The mixture was stirred at room temperature for 15 hours. Then, 109.9 mg of the peptide resin was exposed to 2 ml of cocktail (80 mg of 4-methylmercaptophenol (MMP), 0.2 ml methanol, 1.8 ml trifluoroacetic acid (TFA), 0.1 ml triethylsilane) and the mixture was stirred at room temperature for 2 hours. The peptide was precipitated by tert-butylmethylether. Subsequently, it was dissolved in 10% acetic acid, checked its eluted position on HPLC for analysis through ODS column and purified by conventional preparative HPLC.

The following are the conditions of HPLC for analysis. HPLC: Hitachi L-6200 system, detector: Hitachi L-4000, column: Vydac Protein & Peptide $C_{18}$ (4.6 mm in diameter× 25 cm in length), transfer-phase: 0 to 75% acetonitrile/0.1% TFA, 45 min gradient, flow rate: 1 mil/min., column temperature: room temperature, detective wave: 214 nm.

The following are the conditions of conventional preparative HPLC. HPLC: Waters 600E system, detector: Waters 484, column: Vydac Protein & Peptide $C_{18}$ (20 mm in diameter×25 cm in length), transfer-phase: 0 to 75% acetonitrile/0.1% TFA, 45 min gradient, flow rate: 15 ml/min., column temperature: room temperature, detective wave: 230 nm.

(2) Synthesis of Fragment $P^1$ in SEQ ID NO.:1 of the Sequence Listing

The peptide from C-terminal to the position 17, Asp, was synthesized by the Peptide Synthesizer. After Cys was coupled to N-terminal of the peptide, amino group of Cys was acetylated by 20% acetic anhydride in dichloromethane. Subsequently, 300 mg of the peptide resin was exposed to cocktail (TFA 9 ml, MMP 400 mg, methanol 1 ml, triethylsilane 0.1 ml: room temperature, 2 hours) and was precipitated by tert-butylmethylether.

Then it was dissolved in 10% acetic acid and treated on HPLC according to the above described procedures of Fragment $P^2$.

(3) Synthesis of the Peptide Derivatives 2.5 mg (1.25 μmol) of Fragment $P^2$ of which N-terminal was protected by SMCC was dissolved in 0.3 ml of dimethylformamide (DMF), 0.3 ml of acetonitrile and 0.1 ml of 10% acetic acid. Then, 5.0 mg (2.40 μmol) of Fragment $P^1$ in 0.9 ml of DMF and 2 μmol of EDTA were added to the solution. Then 5.0 mg (2.50 mmol) of Fragment P2 in 0.5 ml of DMF, 0.3 ml of acetonitrile and 0.2 ml of 10% acetic acid were added to the solution and its reaction was checked on HPLC for analysis. Subsequently, the solution was purified on the conventional preparative HPLC. 1.5 mg of the purified synthetic peptide derivative was finally obtained (0.37 μmol, the yield: 15%).

The structure of the obtained synthetic peptide derivative was conformably indicated by the following chemical structure, formula II, by way of amino acid analysis and mass spectroscopic analysis.

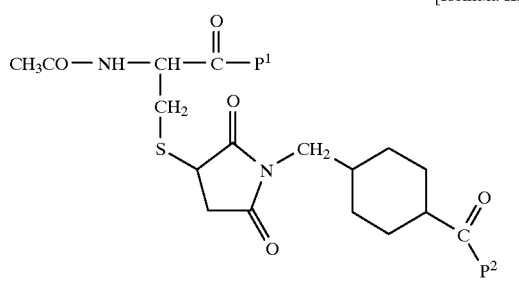

[formula III]

(4) Amino Acid Analysis

After the synthetic peptide derivative was conducted under hydrolysis by 6N HCl (added 4% thioglycolic acid, at 110° C., 24 hours), its composition was investigated by Hitachi Amino Acid Analyzer (Hitachi L8500). The results were shown in Table 1.

TABLE 1

| Amino acid | Actual data | Existing number |
|---|---|---|
| Ala | 3 | (3) |
| Asx | 5.22 | (6) |
| Thr | 0.96 | (1) |
| Ser | 2.61 | (3) |
| Glx | 1.02 | (1) |
| Gly | 1.90 | (2) |
| Val | 4.15 | (5) |
| Ile | 2.31 | (3) |
| Leu | 1.00 | (1) |
| Tyr | 0.89 | (1) |
| Phe | 0.90 | (1) |
| Trp | 1.03 | (1) |
| Lys | 1.93 | (2) |
| Pro | 2.74 | (3) |

(5) Mass Spectroscopic Analysis

The molecular weight of the synthetic peptide derivative which was determined by mass spectroscopic analysis entrusting Takara Shuzo Co., Ltd. was 4083.24 (±0.3) with reference to that of 4083.65 in theory.

Example 2

Assay of BMP Inhibiting Activity

BMP-2 antagonist-like activity of the present synthetic peptide derivative thus obtained in example 1 was assayed by way of cultured MC3T3-E1 cells which were established from mouse calvaria according to its osteoblast-like property by Kodama et al. The cultured MC3T3-E1 cells were prepared according to Takuwa et al., $5 \times 10^4$ cells/cm$^2$ of the cultured cells in serum-free α-MEM culture broth containing 0.3% bovine serum albumin were treated with various concentrations of the present synthetic peptide derivative and recombinant human BMP-2 (rh-BMP-2) for 2 days so as to assay ALPase activity by colorimetry on p-nitrophenyl phosphate.

As shown in Table 2, 5 ng/ml of rh-BMP-2 increased ALPase activity in MC3T3-E1 cells by 3 folds in comparison with a control group. The present synthetic peptide derivative inhibited ALPase activity in MC3T3-E1 cells which were promoted by rh-BMP-2 with $2 \times 10^{-9}$ to $2 \times 10^{-6}$ M dose dependently.

TABLE 2

| Compound added | ALPase activity (pmol/min) |
|---|---|
| Control | 305 ± 36 |
| rh-BMP-2 (5 ng/ml) | 892 ± 52 |
| rh-BMP-2 (5 ng/ml) + synthetic peptide derivative (2 × 10$^{-10}$ M) | 876 ± 120 |
| rh-BMP-2 (5 ng/ml) + synthetic peptide derivative (2 × 10$^{-9}$ M) | 632 ± 71 |
| rh-BMP-2 (5 ng/ml) + synthetic peptide derivative (2 × 10$^{-8}$ M) | 486 ± 36 |
| rh-BMP-2 (5 ng/ml) + synthetic peptide derivative (2 × 10$^{-7}$ M) | 302 ± 54 |
| rh-BMP-2 (b ng/ml) + synthetic peptide derivative (2 × 10$^{-6}$ M) | 269 (n = 1) | mean ± standard vriation, n = 4

The synthetic peptide derivatives in this invention can be used as a medical agent to inhibit the progress of symptoms of ectopic ossification and arterial sclerosis. They can also be used as a treatment for BMP expressed bone and cartilage tumor, and a prevention for ossification of soft parts tissue around ligamentum and bone. When abnormal bone metabolization is progressed, such as Paget's disease, it can inhibit the progress of symptoms by degrading the function of osteoblasts. It is also effective for screening or evaluating reagents for peptide or low molecular chemical medicines started from BMP that compete with the binding of BMP and the receptors.

What is claimed is:

1. A peptide derivative represented by the formula $$P^1\text{-}R^1\text{-}P^2$$

wherein $P^1$ is a peptide having an amino acid sequence in the SEQ ID NO.:1 of the Sequence Listing, or analogoues thereof; $P^2$ is a peptide having an amino acid sequence in the SEQ ID NO.:2 of the Sequence Listing, or analogues thereof; $R^1$ denotes a linker comprising organic groups having carboxyl groups at both ends that enable to bind N-terminal of the above described peptides keeping a suitable distance between the peptides, or pharmaceutically acceptable salts thereof.

2. The peptide derivative according to claim 1 wherein a linker $R^1$ can be any compound with a property that does not interfere with the activity of the each peptide $P^1$ and $P^2$ and is represented by the following formula I or formula II:

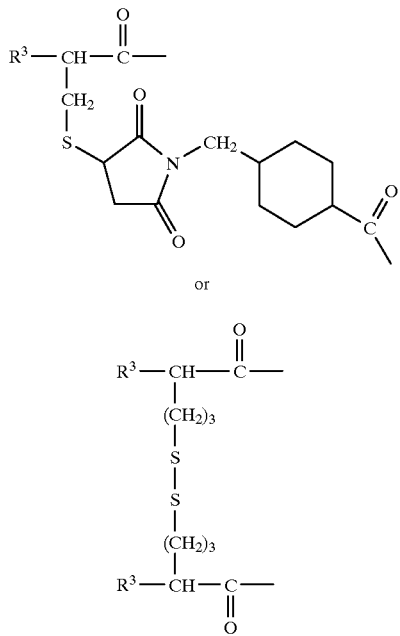

or a pharmaceutically acceptable salt thereof wherein $R^3$ is $CH_3CO-NH-$ or either one of hydrogen, alkyl, aryl, alkanolylamino or aryloylamino or a pharmaceutically acceptable salt thereof.

3. An analogue of the peptide derivative of claim 1 or 2, wherein the amino acid sequence of $P^1$ is selected from the group consisting of SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, and SEQ ID NO:14.

4. An analogue of the peptide derivative of claim 1 or 2, wherein the amino acid sequence of $P^2$ is selected from the group consisting of SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, and SEQ ID NO:26.

5. A pharmaceutical composition for an antagonist to bone morphogenetic proteins (BMP) comprising a peptide according to claim 3 or a pharmaceutically acceptable salt thereof, and a pharmaceutically acceptable carrier.

6. A pharmaceutical composition for an antagonist to bone morphogenetic proteins (BMP) comprising a peptide according to claim 4 or a pharmaceutically acceptable salt thereof, and a pharmaceutically acceptable carrier.

7. A method of treating or preventing ectopic ossification, ectopic bone formation or metabolic diseases accompanied by calcification which comprises a pharmaceutical carrier and an effective amount of a peptide derivative according to claim 3.

8. A method of treating or preventing ectopic ossification, ectopic bone formation or metabolic diseases accompanied by calcification which comprises a pharmaceutical carrier and an effective amount of a peptide derivative according to claim 4.

* * * * *